US008986537B2

(12) United States Patent
Sircar et al.

(10) Patent No.: US 8,986,537 B2
(45) Date of Patent: Mar. 24, 2015

(54) PRODUCTION OF NON-CARCINOGENIC BRIGHTSTOCK EXTRACTS

(71) Applicant: ExxonMobil Research and Engineering Company, Annandale, NJ (US)

(72) Inventors: Cristina M. Sircar, Falls Church, VA (US); Keith K. Aldous, Winchester, VA (US); James J. Freeman, Hopewell, NJ (US); Katy O. Goyak, Easton, PA (US)

(*) Notice: Subject to any disclaimer, the term of this patent is extended or adjusted under 35 U.S.C. 154(b) by 215 days.

(21) Appl. No.: 13/803,454

(22) Filed: Mar. 14, 2013

(65) Prior Publication Data
US 2014/0262958 A1    Sep. 18, 2014

(51) Int. Cl.
*G01N 33/28*    (2006.01)

(52) U.S. Cl.
CPC .................................. *G01N 33/2823* (2013.01)
USPC ................. 208/309; 208/86; 208/87; 208/88; 208/94; 208/96; 208/97; 208/177; 208/314; 208/347; 208/354; 435/29; 435/30; 435/34

(58) Field of Classification Search
CPC ........................................... G01N 33/00–33/98
USPC ........... 208/86–88, 94, 96–97, 177, 309, 314, 208/347, 354; 435/29–30, 34
See application file for complete search history.

(56) References Cited

U.S. PATENT DOCUMENTS

| | | |
|---|---|---|
| 4,499,187 A | 2/1985 | Blackburn et al. |
| 5,034,119 A | 7/1991 | Blackburn et al. |
| 5,178,747 A | 1/1993 | Blackburn et al. |
| 5,308,470 A | 5/1994 | Blackburn et al. |
| 6,410,816 B2 | 6/2002 | Takasaki et al. |
| 2001/0045377 A1 | 11/2001 | Morishima et al. |

FOREIGN PATENT DOCUMENTS

WO        9300414        1/1993

OTHER PUBLICATIONS

Mehrotra, "A simple equation for predicting the viscosity of crude oil fractions", Chemical Engineering Research and Design (1995), 73(A1), pp. 87-90; ISSN: 0263-8762.

(Continued)

*Primary Examiner* — Brian McCaig
(74) *Attorney, Agent, or Firm* — Robert A Migliorini; Larry Carter

(57) ABSTRACT

Provided are multiple correlations for relationships between MI value for a brightstock extract and the distillation cut point temperature used for separation of the vacuum resid that is used to form the brightstock extract. Based on these correlations, a BSE having a desired MI value can be formed based on an adjustment of the distillation cut point temperature. A first correlation establishes a relationship between a fractional weight boiling temperature for a vacuum resid fraction and a distillation cut point temperature for separating the vacuum resid fraction from at least one distillate fraction in a feedstock. A second correlation establishes a relationship between a fractional weight boiling temperature for a brightstock extract derived from the vacuum resid fraction, and the fractional weight boiling temperature for the vacuum resid fraction. A third correlation has been established between the fractional weight boiling temperature for the brightstock extract and a mutagenicity index value.

19 Claims, 3 Drawing Sheets

(56) References Cited

OTHER PUBLICATIONS

Wang et al., "A study on the relationship between the composition and the usage of asphaltic heavy oil", ACS 203rd National Meeting (San Francisco Apr. 5-10, 1992) ACS Division of Petroleum Chemistry Preprints V37 N.3 933-36 (Apr. 1992).

Oyekunle, "A two parameter correlation for petroleum bitumens", Petroleum Science and Technology (2000), 18 (1 & 2), 63-79; ISSN: 1091-6466.

Plummer et al., "Asphalt Quality and Yield Predictions From Crude Oil Analyses", Assoc. Asphalt Paving Technol. Tech. Sessions (Scottsdale, Ariz. Apr. 9-11, 1984) Proc. Assoc. Asphalt Paving Technol. V53 138-59 (1984).

Michon et al., "Asphalt Study by Neuronal Networks. Correlation between Chemical and Rheological Properties", Energy & Fuels (1997), 11(6), 1188-1193; ISSN: 0887-0624.

Silvia et al., "Asphalt's performance grades estimation using artificial Neural Networks and proton nuclear Magnetic Resonance spectroscopy", Vision Tecnologica (2001), 9(1), 17-24; ISSN: 1315-0855; English Abstract Only.

Pauli et al., "Assessment of physical property prediction based on asphalt average molecular structures", ACS Division of Petroleum Chemistry, Inc. Preprints (American Chemical Society, ACS 229th ACS National Meeting, San Diego, CA Mar. 13, 2005-Mar. 17, 2005) 50/2 255-259 (Mar. 2005).

Laxalde et al., "Characterisation of heavy oils using near-infrared spectroscopy: Optimisation of pre-processing methods and variable selection", Analytica Chimica Acta (2011), 705(1-2), 227-234; ISSN: 0003-2670.

Kyriacou et al., "Characterization of oil residual fractions using intrinsic viscosity measurements", Fuel (1988), 67(1), 109-13; ISSN: 0016-2361.

Jimenez-Mateos et al., "Characterization of petroleum bitumens and their fractions by thermogravimetric analysis and differential scanning calorimetry", 26th Fine Particle Society Annual Meeting (Chicago 1995) Fuel V75 N.15 1691-700 (Dec. 1996).

Lima et al., "Determination of asphalt cement properties by near infrared spectroscopy and chemometrics", Petroleum Science and Technology 22/5-6 589-600 (May/Jun. 2004).

Lu, "Establishment of mathematical models for physical properties of vacuum residue and simulation", Lianyou Sheji (1997), 27(4), 34-36 CODEN: LISHEM; ISSN: 1002-106X; English Abstract Only.

Satya et al., "Estimation of Properties of Crude Oil Residual Fractions Using Chemometrics", Energy & Fuels (2007), 21(2), pp. 998-1005; ISSN: 0887-0624.

Miadonye et al., "Generalized oil viscosity model for the effects of temperature, pressure and gas composition", Journal of Canadian Petroleum Technology (1997), 36(1), pp. 50-54; ISSN: 0021-9487.

Romatier et al., "Heavy crude and residue processing", Dev. Pet. Refin., Symp. (1982), II.1/1-II.1/12 Inst. Chem. Eng., Rugby, UK.

Sanchez Caba et al., "Manufacture of bitumens from mixtures of crudes. Prediction of their properties", Ingenieria Quimica (Madrid) (1997), 29(335), 77-81 CODEN: INQUDI; ISSN: 0210-2064; English Abstract Only.

Orrego-Ruiz et al., "Mid-infrared Attenuated Total Reflectance (MIR-ATR) Predictive Models for Asphaltene Contents in Vacuum Residua: Asphaltene Structure-Functionality Correlations Based on Partial Least-Squares Regression (PLS-R)", Energy & Fuels (2011), 25(8), 3678-3686; ISSN: 0887-0624.

Linan et al., "Molecular Distillation of Petroleum Residues and Physical-Chemical Characterization of Distillate Cuts Obtained in the Process", Journal of Chemical & Engineering Data (2010), 55(9), pp. 3068-3076; ISSN: 0021-9568.

Bahia et al., "Non-linear viscoelastic and fatigue properties of asphalt binders", Asphalt Paving Technology (1999), 68, pp. 1-34; ISSN: 0270-2932.

de Peinder et al., "Partial least squares modeling of combined infrared, 1H NMR and 13C NMR spectra to predict long residue properties of crude oils", Vibrational Spectroscopy (2009), 51(2), 205-212; ISSN: 0924-2031.

Laux et al., "Particle distribution, colloidal stability, and rheology of crude oil distillation residues and bitumen", Erdoel Erdgas Kohle V109 N.9 368-72 (Sep. 1993); English Abstract Only.

Wahhab et al., "Prediction of asphalt rheological properties using HP-GPC", Journal of Materials in Civil Engineering (1999), 11(1), 6-14; ISSN: 0899-1561.

Orrego-Ruiz et al., "Quality Prediction from Hydroprocessing through Infrared Spectroscopy (IR)", Energy & Fuels (2012), 26(1), pp. 586-593; ISSN: 0887-0624.

Nelson, "Questions on Technology/Estimating Yields of Asphalt in Crude Oil . . . Again", Oil Gas J V66 N.16 93 (Apr. 15, 1968).

Halstead, "Relation of Asphalt Chemistry to Physical Properties and Specifications", Assoc. Asphalt Paving Technol. Tech. Sessions (San Antonio Feb. 11-13, 1985) Proc. Assoc. Asphalt Paving Technol. V54 91-117 (1985).

Zerlia, "Some experimental data on the prediction of macroscopic properties [of heavy petroleum fractions]", La Rivista dei Combustibili V48 N.11-12 459-66 (Nov.-Dec. 1994); English Abstract Only.

Huynh et al., "Structure parameter analyses of asphalt fractions by a modified mathematical approach", Analytical Chemistry (1978), 50(8), 1212-18; ISSN: 0003-2700.

Evdokimova et al., "The effect of the feedstock quality on the (service) properties of road bitumens", Khimiya i Tekhnologiya Topliv i Masel N.4 11-13 (1990); English Abstract Only.

Garrick, "Use of gel-permeation chromatography in predicting properties of asphalt", Journal of Materials in Civil Engineering (1994), 6(3), 376-89; ISSN: 0899-1561.

Wakabayashi, "Viscosity correlation with specific gravity and molecular weight of crude oil fractions", Fuel (1997), 76 (11), pp. 1049-1056; ISSN: 0016-2361.

Baltatu et al., "Viscosity of defined and undefined hydrocarbon liquids calculated using an extended corresponding-states model", International Journal of Thermophysics (1996), 17(1), pp. 213-221; ISSN: 0195-928X.

Jaciel et al., Walther's equation and its applicability in rheology, Revista del Instituto Mexicano de Ingenieros Quimicos (2007), 48(5-6), 47-59; ISSN: 0188-7319; English Abstract Only.

US 8,986,537 B2

PRODUCTION OF NON-CARCINOGENIC BRIGHTSTOCK EXTRACTS

FIELD

Systems and methods are provided for production of non-carcinogenic brightstock extracts.

BACKGROUND

Industry standards are periodically updated to reflect new recommendations for petroleum products, such as a standard associated with possible carcinogenic classifications of aromatic extracts. The mutagenicity index (MI) is typically used to define the carcinogenicity of an aromatic extract. Testing a product stream for its MI value to ensure that the MI value is less than a particular value defined in a standard, however, is time consuming and impractical, as aromatic extract would need to be tested for each batch or product. Therefore, it would be advantageous to avoid the time-consuming testing involved in determining the MI value of an aromatic extract.

U.S. Pat. No. 5,034,119 describes a process for establishing a functional relationship between a mutagenicity index and a physical property correlative of hydrocarbon type for the bright stock extract or deasphalted oil to produce non-carcinogenic bright stock extracts and/or deasphalted oils. The functional relationship results in a product having a mutagenicity index of less than 1.0. Process conditions are established so that a product stream achieving the desired physical property level can be produced.

SUMMARY

In an aspect, a method for producing a brightstock extract is provided. The method includes establishing a first correlation between a) a fractional weight boiling temperature for a brightstock extract derived from a resid fraction, and b) a distillation cut point temperature for separating the resid fraction from a feedstock, comprising the vacuum resid fraction and at least one distillate fraction, where the first correlation has a linear correlation slope of 0.5 or less; establishing a second correlation between the fractional weight boiling temperature for a brightstock extract and a mutagenicity index value; selecting, based on the first correlation and the second correlation, a distillation cut point temperature corresponding to a mutagenicity index for a brightstock extract of 0.5 or less; distilling a feedstock at the selected distillation cut point temperature to separate one or more distillate fractions from a resid fraction; deasphalting the resid fraction to form a deasphalted oil fraction; and performing a solvent extraction on the deasphalted oil to form a brightstock extract fraction having the mutagenicity index of 0.5 or less.

In another aspect, a method for producing a brightstock extract is provided. The method includes selecting a distillation cut point temperature between a resid fraction and one or more distillate fractions, the distillation cut point temperature corresponding to a mutagenicity index value of 0.5 or less for a brightstock extract formed from the resid fraction, the distillation cut point temperature being based on, (a) a first correlation between a fractional weight boiling temperature for a vacuum resid fraction and a distillation cut point temperature for separating the vacuum resid fraction from a feedstock, (b) a second correlation between a fractional weight boiling temperature for a brightstock extract derived from the vacuum resid fraction, and the fractional weight boiling temperature for the vacuum resid fraction, wherein the first correlation has a linear correlation slope of 0.90 or less, and (c) a third correlation between the fractional weight boiling temperature for the brightstock extract and a mutagenicity index value; passing a feedstock through a distillation tower to produce the one or more distillate fractions and the resid fraction at the selected distillation cut point temperature between the resid fraction and the one or more distillate fractions; passing at least a portion of the resid fraction through a deasphalting unit to produce at least a deasphalted oil fraction; and passing the deasphalted oil fraction through a solvent extraction unit to produce at least a brightstock extract having a mutagenicity index value of 0.5 or less.

DETAILED DESCRIPTION

All numerical values within the detailed description and the claims herein are modified by "about" or "approximately" the indicated value, and take into account experimental error and variations that would be expected by a person having ordinary skill in the art.

Overview

In various embodiments, methods are provided for producing a brightstock extract (BSE) with a desired mutagenicity index value, such as a value that meets a current standard or recommendation for a residual aromatic extract. For example, the petroleum industry (CONCAWE) recently made a recommendation that residual aromatic extracts be considered as a possible human carcinogen, classified as H351, or suspected of causing cancer, if a residual aromatic extract has a mutagenicity index (MI) of greater than 0.4. Testing a residual aromatic extract to determine its MI value based on ASTM E 1687-04 is time consuming, taking days to complete for each batch of product. However, other types of predictive testing, if available, may be used to demonstrate that a residual aromatic extract is not carcinogenic. In various embodiments, methods are provided as an alternative to testing each batch to determine the MI value of the residual aromatic extract.

Figure 2:
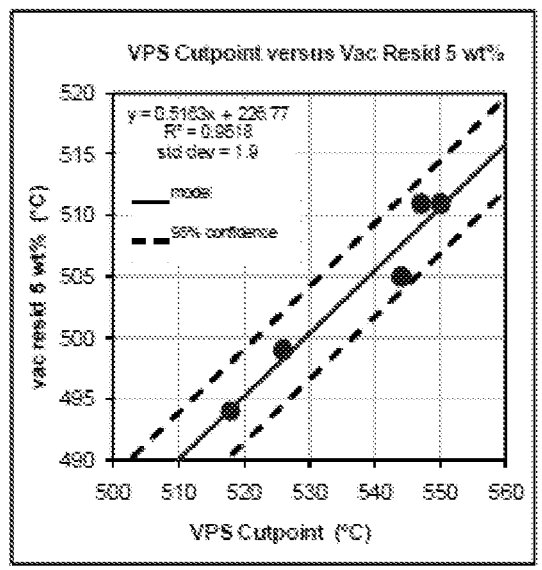
FIG. 2 shows a data plot of a correlation between the 5 wt % fractional weight boiling temperature for a vacuum resid fraction and a distillation cut point temperature for separating the vacuum resid fraction from at least one distillate fraction in a feedstock. The correlation in FIG. 2 is a linear correlation of the form vac resid GCD 5 wt % (° C.)=0.5163*[distillate cut point temperature (° C.)]+226.77, with a standard deviation of +/−1.9° C., which corresponds to a 95% confidence interval of +/−3.8° C. (GCD=Gas Chromatographic Distillation)
Figure 3:
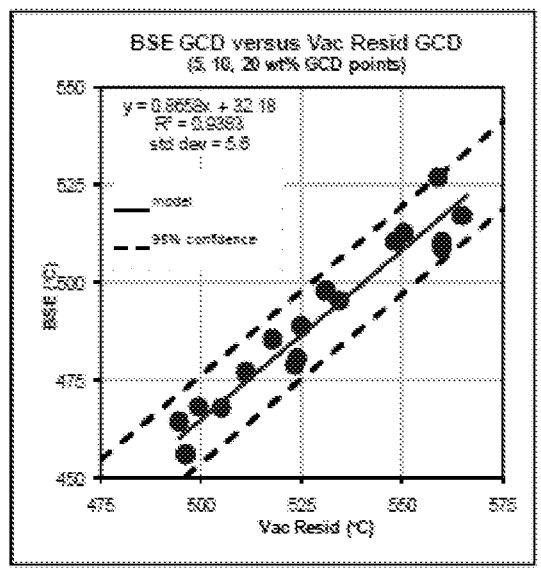
FIG. 3 shows a data plot of a correlation between the 5 wt %, 10 wt % and 20 wt % fractional weight boiling temperatures for a brightstock extract derived from the vacuum resid fraction, and the fractional weight boiling temperature for the vacuum resid fraction. The correlation in FIG. 3 is a linear correlation of the form BSE GCD X wt % (° C.)=0.8658*vac resid GCD X wt % (° C.)+32.18, where X corresponds to 5 wt %/, 10 wt %, or 20 wt %, with a standard deviation of +/−5.6° C., which corresponds to a 95% confidence interval of +/−11.2° C.
Figure 4:
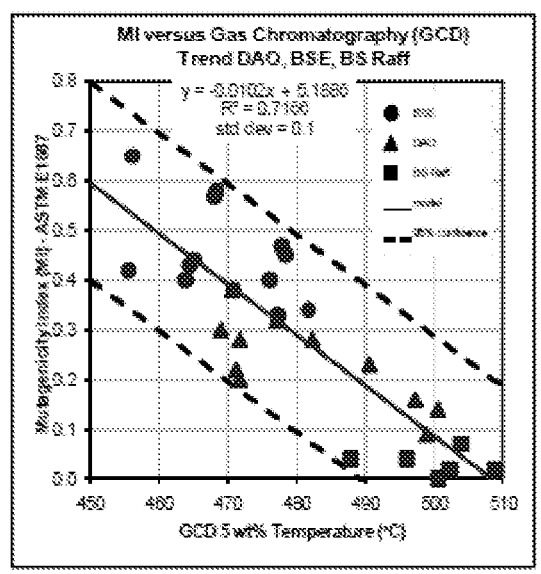
FIG. 4 shows a data plot of a correlation between the 5 wt % fractional weight boiling temperature for various petroleum fractions and a mutagenicity index value. The correlation in FIG. 3 is a linear correlation of the form MI=−0.0102*BSE GCD 5 wt % (° C.)+5.1886, with a standard deviation of +/−0.1 MI, which corresponds to a 95% confidence interval of +/−0.2 MI.

In various aspects, multiple correlations have been developed in order to provide a relationship between the MI value for a brightstock extract and the distillation cut point temperature used for separation of the vacuum resid that is used to form the brightstock extract. Based on these correlations, a BSE having a desired MI value can be formed based on an adjustment of the distillation cut point temperature. A first correlation establishes a relationship between a fractional weight boiling temperature for a vacuum resid fraction and a distillation cut point temperature for separating the vacuum resid fraction from at least one distillate fraction in a feedstock. This first correlation has a linear correlation slope of less than 0.6, or less than 0.55, or preferably 0.52 or less. As an example, FIG. 2 shows a linear correlation slope of 0.5, and specifically 0.52. A second correlation establishes a relationship between a fractional weight boiling temperature for a brightstock extract derived from the vacuum resid fraction, and the fractional weight boiling temperature for the vacuum resid fraction. The second correlation has a linear correlation slope of less than 0.95, or less than 0.90, or preferably 0.87 or less. As an example, FIG. 3 shows a linear correlation slope of 0.9, and specifically 0.87. A third correlation has been established between the fractional weight boiling temperature for the brightstock extract and a mutagenicity index value. The third correlation has a linear correlation slope of greater than −0.02, or greater than −0.015, or preferably greater than −0.011. As an example, FIG. 4 shows a linear correlation slope of −0.01.

Feedstocks

A wide range of petroleum and chemical feedstocks can be processed in accordance with the disclosure. Suitable feedstocks include whole and reduced petroleum crudes, atmospheric and vacuum residua, and deasphalted residua, e.g., brightstock. Other feedstocks can also be suitable, so long as the feedstock includes an appropriate fraction for formation of a brightstock.

One way of defining a feedstock is based on the boiling range of the feed. One option for defining a boiling range is to use an initial boiling point for a feed and/or a final boiling point for a feed. Another option, which in some instances may provide a more representative description of a feed, is to characterize a feed based on the amount of the feed that boils at one or more temperatures. For example, a "T5" boiling point for a feed is defined as the temperature at which 5 wt % of the feed will boil off. Similarly, a "T95" boiling point is a temperature at 95 wt % of the feed will boil. Such a boiling point can be referred to as a fractional weight boiling point. A fractional weight boiling point, corresponding to the percentage of a feed that will boil at a given temperature, can be determined, for example, by the method specified in ASTM D2887. Generally, this can include determining a fractional weight boiling point via gas chromatographic distillation (GCD).

Typical feeds include, for example, feeds with an initial boiling point of at least 650° F. (343° C.), or at least 700° F. (371° C.), or at least 750° F. (399° C.). Alternatively, a feed may be characterized using a T5 boiling point, such as a feed with a T5 boiling point of at least 650° F. (343° C.), or at least 700° F. (371° C.), or at least 750° F. (399° C.). In some aspects, the final boiling point of the feed can be at least 1100° F. (593° C.), such as at least 1150° F. (621° C.), or at least 1200° F. (649° C.), or at least 1499° F. (815° C.). In other aspects, a feed may be used that is a vacuum resid or bottoms fraction, or that otherwise contains a majority of molecules that are typically found in a vacuum resid. Such feeds include, for example, feeds with an initial boiling point of at least 1000° F. (538° C.), or at least 1050° F. (566° C.), or at least 1100° F. (593° C.), or at least 1150° F. (621° C.). Alternatively, a feed may be characterized using a T5 boiling point, such as a feed with a T5 boiling point of at least 1050° F. (566° C.), or at least 1100° F. (593° C.), or at least 1150° F. (621° C.). It is noted that feeds with still lower initial boiling points and/or T5 boiling points may also be suitable, so long as sufficient higher boiling material is available so that a brightstock raffinate can be formed and subsequently solvent dewaxed.

If a broader boiling range feed is used, the feedstock can initially be distilled to form a vacuum resid. The cut point for separating the vacuum resid from other distillate portions of the feed can correspond to any of the T5 boiling points described above. The vacuum resid can then be deasphalted to form a deasphalted oil. The deasphalted oil can then be solvent processed to extract aromatics. This results in a brightstock raffinate and a brightstock extract. The brightstock raffinate can then be solvent dewaxed to form a brightstock basestock and petrolatum. The petrolatum can have a wax content of at least 70 wt %, such as at least 75 wt %, or at least 80 wt %.

In some aspects, the sulfur content of the feed can be at least 300 ppm by weight of sulfur, or at least 1000 wppm, or at least 2000 wppm, or at least 4000 wppm, or at least 10,000 wppm, or at least 20,000 wppm. In other embodiments, including some embodiments where a previously hydrotreated and/or hydrocracked feed is used, the sulfur content can be 2000 wppm or less, or 1000 wppm or less, or 500 wppm or less, or 100 wppm or less.

Distillation Cut Point and Feed Fractionation

In various embodiments, a BSE having a desired MI value is produced from a feedstock. As mentioned, according to the correlations developed for use in embodiments, the MI value of the BSE is dependent upon the distillation cut point temperature for separating a vacuum resid fraction from at least one distillate fraction in a feedstock. While embodiments provide for adjustment of the distillation cut point temperature between the vacuum resid fraction and a distillate fraction to control the MI value of the BSE, cut points in a distillation tower will be generally discussed below.

As an initial process, a suitable feedstock can be separated to form at least a distillate boiling range portion and a bottoms portion. Such a separation can be performed, for example, using a vacuum distillation tower. One method for determining the amounts in the various portions is by selecting cut point temperatures. The cut point temperatures may vary depending on the nature of the feedstock. Generally, cut point between the distillate boiling portion and the bottoms portion can be between 950° F. (510° C.) and 1150° F. (621° C.), such as less than 1100° F. (593° C.). It is noted that the above fractionation temperatures represent the split between a distillate portion and a bottoms portion. If desired, additional fractions could also be formed based on additional cut points.

Another factor in selecting a cut point temperature for fractionating a feedstock is the MI value of the brightstock extract. The correlations used to predict the MI value of the brightstock extract are described below.

Overall Process Flow

To produce a brightstock extract having a mutagenicity index value below a particular threshold, various processes are utilized. While any lubricant refinery that utilizes a solvent extraction step and/or a deasphalting step to produce a brightstock extract is contemplated for use in various embodiment, a vacuum distillation tower, followed by a deasphalting unit, followed by a solvent extractions unit will be described for exemplary purposes.

A feedstock for brightstock extract production, as described above, is introduced into a vacuum distillation tower. In one embodiment, the feedstock is a reduced crude, such that the lighter compounds have already been boiled off under atmospheric pressure. The vacuum distillation tower fractionates the feedstock into at least a distillate portion and a bottoms portion (i.e., a vacuum resid). For example, in the vacuum distillation tower, light ends are removed from the uppermost portion of the distillation tower and one or more distillate fractions are produced, including, for instance, a light, intermediate, and heavy distillate fractions. Vacuum resid exits through the bottom of the distillation tower. At least a portion of the vacuum resid is passed to a deasphalting unit, where it is treated by any of a number of processes. Generally, the deasphalting unit separates asphalt from crude oil. In one embodiment, the deasphalting unit is a solvent deasphalting unit, which separates the asphalt from the feedstock. One such process of treating the vacuum resid with a solvent is propane deasphalting, which uses propane as the solvent. While propane deasphalting is mentioned, other processes are contemplated to be within the scope of the present disclosure. In addition to asphalt, the deasphalting unit also produces a deasphalted oil.

As discussed above, the distillation cut point temperature is the temperature at which a vacuum resid fraction is separated from at least one distillate fraction in a feedstock. The MI value of a brightstock extract, according to embodiments described herein, is dependent upon the distillation cut point temperature in the vacuum distillation tower. The correlations used to predict the distillation cut point temperature based on the desired MI value of the brightstock extract are discussed in detail below.

The deasphalted oil is sent for further processing into a solvent extraction unit, where it is treated with any one of a number of suitable solvents or solvent combinations to remove undesirable constituents by preferential solution to produce a lubricant brightstock raffinate. In addition to an aromatics-reduced brightstock raffinate, a brightstock extract is also produced, and using embodiments described herein, the aromatics-rich brightstock extract will have a desired MI value.

Figure 1:
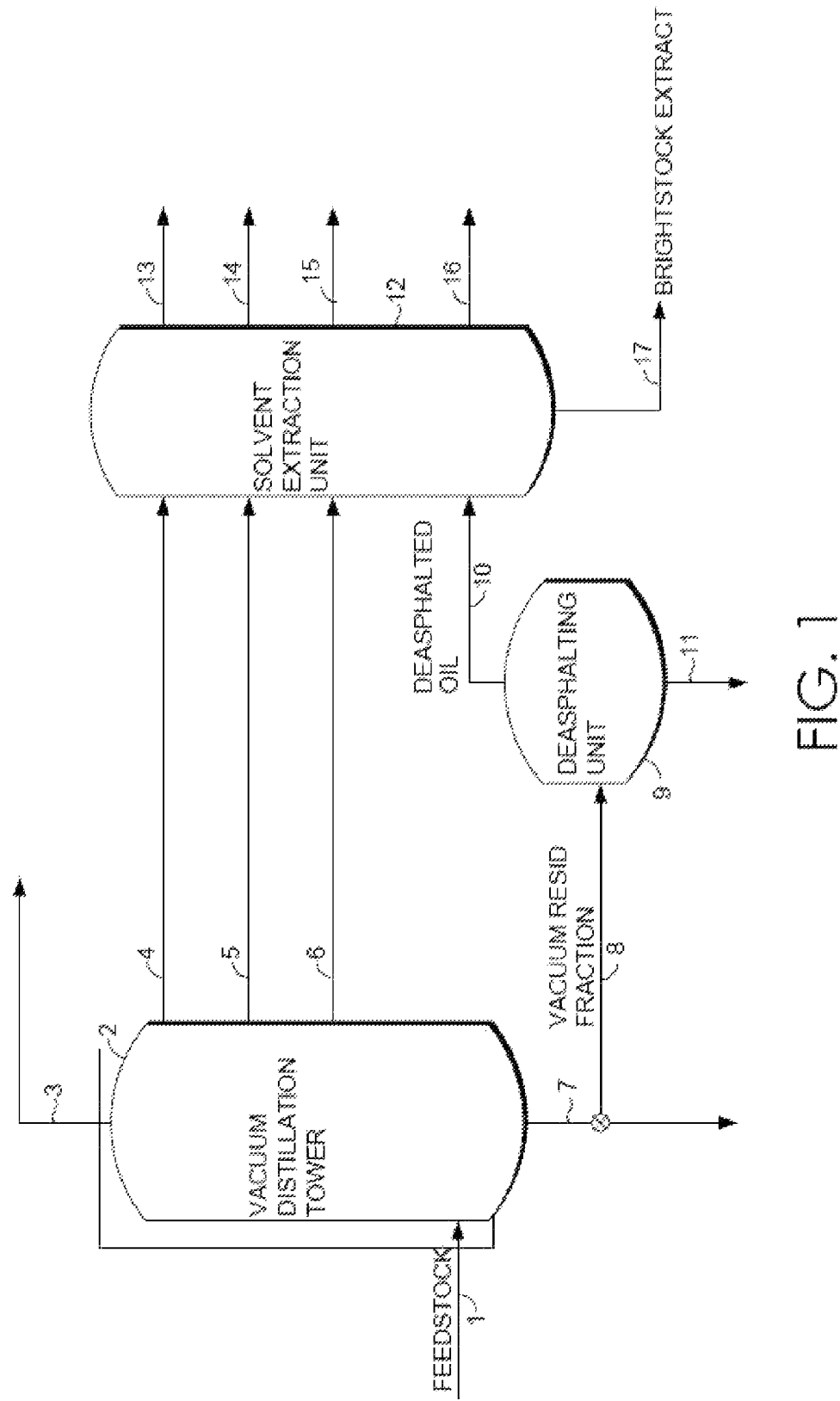
FIG. 1 schematically shows an example of a configuration suitable for producing a brightstock extract having a desired mutagenicity index value.

To illustrate an exemplary process flow, FIG. 1 is provided. For instance, FIG. 1 illustrates feedstock 1 fed into a vacuum distillation tower 2, where light ends 3 and multiple distillate fractions 4, 5, and 6 are produced. Also produced is a vacuum resid 7, wherein at least a fraction of this vacuum resid 8 is fed into a deasphalting unit 9 to produce asphalt 11 and a deasphalted oil 10. The deasphalted oil 10 is then fed into a solvent extraction unit 12, where multiple oil raffinates 13, 14, and 15 are produced. A brightstock raffinate 16 and a brightstock extract 17 are also produced. As mentioned, as per embodiments described herein, the brightstock extract 17 will have the desired MI value based on the distillation cut point temperature between the vacuum resid and a distillate fraction in the vacuum distillation tower.

Correlations to Predict the Mutagenicity Index Value of a Brightstock Extract

Multiple correlations have been developed to predict the MI value of the BSE based on an adjustment of the distillation cut point temperature for separating the vacuum resid fraction from at least one distillate fraction in a feedstock. A first correlation, shown in FIG. 2, illustrates a relationship between a fractional weight boiling point temperature for a vacuum resid fraction and a distillation cut point temperature for separating the vacuum resid fraction from at least one distillate fraction in a feedstock. The temperature on the y axis of the plot is the fractional weight boiling point temperature, or more specifically, the 5 wt % fractional weight boiling point temperature of a vacuum resid. As used herein, the fractional weight boiling point temperature is the temperature at which a given fraction of a feed will boil when performing gas chromatographic distillation. As is the case of FIG. 2, the 5 wt % fractional weight boiling point temperature of a vacuum resid is the temperature at which 5 wt % of the feed will boil. In this discussion, fractional weight boiling points are determined using a gas chromatographic distillation.

FIG. 2 illustrates a linear correlation slope, representing the relationship between the 5 wt % fractional weight boiling point temperature and the distillation cut point temperature. It should be noted that a correlation between two temperatures can have any convenient functional form. For the purpose of this description of the first correlation, the characteristics of fitting a correlation will be based on a linear functional form. As such, in this disclosure, the relation between two temperatures will be discussed as being based on a linear correlation slope. The first correlation shown in FIG. 2 has a linear correlation slope of less than 0.6, or less than 0.55, or preferably less than 0.52. The correlation in FIG. 2 is a linear correlation of the form vac resid GCD 5 wt % (° C.)=0.5163*[distillate cut point temperature (° C.)]+226.77, with a standard deviation of +/−1.9° C., which corresponds to a 95% confidence interval of +/−3.8° C. However, as mentioned, the precise slope represented by this equation does not define the disclosure, but rather the relationship between the fractional weight boiling point temperature and the distillation cut point temperature.

In FIG. 2, both the mean value of the linear correlation slope and error bars corresponding to the 95% confidence interval are shown. When using FIG. 2 to select a minimum cut point temperature for achieving a desired 5 wt % boiling point for a vacuum resid, one option is to use the mean value. Another option is to use one of the 95% confidence interval values, in order to allow for variations for a particular feedstock.

A second correlation, shown in FIG. 3, establishes a relationship between a fractional weight boiling temperature for a BSE derived from a vacuum resid fraction, and the fractional weight boiling temperature for the vacuum resid fraction. In the correlation shown in FIG. 3, the data points shown are for 5 wt %, 10 wt %, and 20 wt % fractional weight boiling points for a BSE that is formed by performing an aromatics extraction on a vacuum resid fraction. This is shown in comparison with the 5 wt %, 10 wt %, and 20 wt % fractional weight boiling points for the vacuum resid. As described above, a BSE is produced by passing at least a portion of a vacuum resid produced from a feedstock through a deasphalting unit to produce a deasphalted oil, which is passed through a solvent extraction unit. The sampling for the data points shown in FIG. 3 was taken from six different vacuum resids, and as such the data points represent a population of brightstock extracts from different crude sources. FIG. 3 shows that the correlation between the fractional weight boiling point for a brightstock extract and the fractional weight boiling point for a corresponding vacuum resid has a low or minimal dependence on the nature of the feed.

The second correlation has a linear correlation slope of less than 0.95, or less than 0.90, or preferably less than 0.87. More particularly, the correlation in FIG. 3 is a linear correlation of the form BSE GCD X wt % (° C.)=0.8658*vac resid GCD X wt % (° C.)+32.18, where X corresponds to 5 wt %, 10 wt %, or 20 wt %, with a standard deviation of +/−5.6° C., which corresponds to a 95% confidence interval of +/−11.2° C. The precise slope represented by this equation does not define the disclosure, but rather the relationship between the fractional weight boiling temperature for a BSE derived from a vacuum resid fraction, and the fractional weight boiling temperature for the vacuum resid fraction. It has been unexpectedly discovered that the correlation between the fractional weight boiling temperature for a BSE and the fractional weight boiling temperature for the corresponding vacuum resid fraction is less than a 1:1 correlation, as shown by the slope in FIG. 3. In the specific case of FIG. 3, for every one degree increase of a fractional weight boiling temperature (5 wt %, 10 wt %, or 20 wt %) of a vacuum resid, the corresponding fractional weight boiling temperature of a BSE does not increase by one degree, but instead, increases only by 0.86 degrees. It is noted that the linear correlation slope shown in FIG. 3 is based on forming a correlation for a combined data set using the 5 wt %, 10 wt %, and 20 wt % fractional boiling points. A different linear correlation slope might be identified if the data set was limited to just a single data type, such as only 5 wt % fractional weight boiling points. However, the general nature of the correlation would otherwise be similar.

In FIG. 3, both the mean value of the linear correlation slope and error bars corresponding to the 95% confidence interval are shown. When using FIG. 3 to select a vacuum resid fractional weight boiling temperature for achieving a desired 5 wt % fractional weight boiling point for a brightstock extract, one option is to use the mean value. Another option is to use one of the 95% confidence interval values, in order to allow for variations for a particular feedstock.

As mentioned for the correlation of FIG. 2, FIG. 3 also illustrates a linear correlation slope, but the linear correlation slope of FIG. 3 represents the relationship between the fractional weight boiling temperature for a BSE derived from a vacuum resid fraction, and the fractional weight boiling temperature for the vacuum resid fraction. It should be noted that a correlation between two temperatures can have any convenient functional form. For the purpose of this description of the second correlation, the characteristics of fitting a correlation will be based on a linear functional form. As such, in this disclosure, the relation between two temperatures will be discussed as being based on a linear correlation slope.

In one embodiment, the first and second correlations may be combined, such that the combined correlation illustrates a relationship between a fractional weight boiling temperature for a brightstock extract derived from a vacuum resid fraction, and a distillation cut point temperature for separating the vacuum resid fraction from a feedstock comprising the vacuum resid fraction and at least one distillate fraction. In this instance, the linear correlations slope may be 0.60 or less, or 0.55 or less, or preferably 0.5 or less.

FIG. 4 shows a third correlation between the fractional weight boiling temperature for three different types of feedstocks, including deasphalted oil (DAO), BSE, and brightstock raffinate (BS Raff) and a mutagenicity index. This plot shows that, for these three feedstocks, the MI is dependent on the 5 wt % boiling point but independent of the feed identity. Specifically in FIG. 4, the 5 wt % boiling point is shown on the x axis for each of the three feedstocks. The three feedstocks are related, in that a brightstock extract and brightstock raffinate are the two product streams formed when an aromatics extraction process is performed on a deasphalted (vacuum resid) oil.

This third correlation has a linear correlation slope of greater than −0.02, or greater than −0.015, or preferably greater than −0.011. The correlation in FIG. 3 is a linear correlation of the form MI=−0.0102*BSE GCD 5 wt % (° C.)+5.1886, with a standard deviation of +/−0.1 MI, which corresponds to a 95% confidence interval of +/−0.2 MI. The precise slope represented by this equation does not define the disclosure, but rather the relationship between the fractional weight boiling temperature between three different feedstocks and the MI. In FIG. 4, both the mean value of the linear correlation slope and error bars corresponding to the 95% confidence interval are shown. When using FIG. 4 to select a brightstock extract fractional weight boiling temperature for achieving a mutagenicity index value, one option is to use the mean value. Another option is to use one of the 95% confidence interval values, in order to allow for variations for a particular feedstock. As mentioned for the correlation of FIGS. 2 and 3, a correlation between two temperatures can have any convenient functional form. For the purpose of this description of the third correlation, the characteristics of fitting a correlation will be based on a linear functional form. As such, in this disclosure, the relation between two temperatures will be discussed as being based on a linear correlation slope.

ADDITIONAL EMBODIMENTS

Embodiment 1

A method for producing a brightstock extract, comprising: establishing a first correlation between a) a fractional weight boiling temperature for a brightstock extract derived from a resid fraction, and b) a distillation cut point temperature for separating the resid fraction from a feedstock, comprising the vacuum resid fraction and at least one distillate fraction, where the first correlation has a linear correlation slope of 0.5 or less; establishing a second correlation between the fractional weight boiling temperature for a brightstock extract and a mutagenicity index value; selecting, based on the first correlation and the second correlation, a distillation cut point temperature corresponding to a mutagenicity index for a brightstock extract of 0.5 or less; distilling a feedstock at the selected distillation cut point temperature to separate one or more distillate fractions from a resid fraction; deasphalting the resid fraction to form a deasphalted oil fraction; and performing a solvent extraction on the deasphalted oil to form a brightstock extract fraction having the mutagenicity index of 0.5 or less.

Embodiment 2

The method of Embodiment 1, wherein the first correlation includes: (1) a correlation between a fractional weight boiling temperature for a vacuum resid fraction and a distillation cut point temperature for separating the vacuum resid fraction from a feedstock, and (2) a correlation between a fractional weight boiling temperature for a brightstock extract derived from the vacuum resid fraction, and the fractional weight boiling temperature for the vacuum resid fraction.

Embodiment 3

The method of Embodiment 2, wherein the correlation between the fractional weight boiling temperature for the brightstock extract derived from the vacuum resid fraction, and the fractional weight boiling temperature for the vacuum resid fraction is 0.90 or less.

Embodiment 4

The method of any of the above embodiments, wherein the fractional weight boiling temperature for the vacuum resid fraction is a 5 wt % boiling temperature.

Embodiment 5

The method of any of the above embodiments, wherein the fractional weight boiling temperature for the brightstock extract derived from a resid fraction is one of a 5 wt %, a 10 wt %, or a 20 wt % boiling temperature.

Embodiment 6

The method of any of the above embodiments, wherein the distillation cut point temperature is selected to correspond to a mutagenicity index of less than 0.4.

Embodiment 7

The method of any of the above embodiments, wherein the second correlation has a linear correlation slope of at least −0.015.

Embodiment 8

The method of any of the above embodiments, wherein the second correlation also includes a correlation between a fractional weight boiling temperature for a deasphalted oil and a mutagenicity index value.

Embodiment 9

The method of any of the above embodiments, wherein the second correlation also includes a correlation between a fractional weight boiling temperature for a brightstock raffinate and a mutagenicity index value.

Embodiment 10

The method of any of the above embodiments, wherein the distillation cut point is selected based on a 95% confidence interval of the linear correlation slope for the first correlation.

Embodiment 11

The method of any of the above embodiments, wherein the distillation cut point is selected based on a 95% confidence interval of the linear correlation slope for the second correlation.

Embodiment 12

A method for producing a brightstock extract, the method comprising: selecting a distillation cut point temperature between a resid fraction and one or more distillate fractions, the distillation cut point temperature corresponding to a mutagenicity index value of 0.5 or less for a brightstock extract formed from the resid fraction, the distillation cut point temperature being based on, (a) a first correlation between a fractional weight boiling temperature for a vacuum resid fraction and a distillation cut point temperature for separating the vacuum resid fraction from a feedstock, (b) a second correlation between a fractional weight boiling temperature for a brightstock extract derived from the vacuum resid fraction, and the fractional weight boiling temperature for the vacuum resid fraction, wherein the first correlation has a linear correlation slope of 0.90 or less, and (c) a third correlation between the fractional weight boiling temperature for the brightstock extract and a mutagenicity index value; passing a feedstock through a distillation tower to produce the one or more distillate fractions and the resid fraction at the selected distillation cut point temperature between the resid fraction and the one or more distillate fractions; passing at least a portion of the resid fraction through a deasphalting unit to produce at least a deasphalted oil fraction; and passing the deasphalted oil fraction through a solvent extraction unit to produce at least a brightstock extract having a mutagenicity index value of 0.5 or less.

Embodiment 13

The combination of Embodiment 12 with any of Embodiments 2-11.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

What is claimed is:

1. A method for producing a brightstock extract, comprising:
   establishing a first correlation between
      a) a fractional weight boiling temperature for a brightstock extract derived from a resid fraction, and
      b) a fractional weight boiling temperature of the resid fraction, the resid fraction comprising a vacuum resid fraction separated from a feedstock, the feedstock comprising the vacuum resid fraction and at least one distillate fraction,
      where the first correlation has a linear correlation slope of 0.95 or less;
   establishing a second correlation between the fractional weight boiling temperature for a brightstock extract and a mutagenicity index value;
   selecting, based on the first correlation and the second correlation, a distillation cut point temperature corresponding to a mutagenicity index for a brightstock extract of 0.5 or less;
   distilling a feedstock at the selected distillation cut point temperature to separate one or more distillate fractions from a resid fraction;
   deasphalting the separated resid fraction to form a deasphalted oil fraction; and
   performing a solvent extraction on the deasphalted oil to form a brightstock extract fraction having the mutagenicity index of 0.5 or less.

2. The method of claim 1, wherein the method further comprises:
   establishing a third correlation between the fractional weight boiling temperature for the resid fraction and a distillation cut point temperature for separating the resid fraction from the feedstock, wherein selecting the distillation cut point temperature comprises selecting a distillation cut point temperature based on the first correlation, the second correlation, and the third correlation.

3. The method of claim 2, wherein the third correlation between the fractional weight boiling temperature for the resid fraction and the distillation cut point temperature for separating the resid fraction from the feedstock has a linear correlation slope of 0.60 or less.

4. The method of claim 1, wherein the correlation between the fractional weight boiling temperature for the brightstock extract derived from the vacuum resid fraction, and the fractional weight boiling temperature for the vacuum resid fraction has a linear correlation slope of 0.90 or less.

5. The method of claim 1, wherein the fractional weight boiling temperature for the resid fraction is a 5 wt % boiling temperature.

6. The method of claim 1, wherein the fractional weight boiling temperature for the brightstock extract derived from a resid fraction is one of a 5 wt %, a 10 wt %, or a 20 wt % boiling temperature.

7. The method of claim 1, wherein the distillation cut point temperature is selected to correspond to a mutagenicity index of less than 0.4.

8. The method of claim 1, wherein the second correlation has a linear correlation slope of at least −0.015.

9. The method of claim 1, wherein the second correlation also includes a correlation between fractional weight boiling temperature for a deasphalted oil and a mutagenicity index value.

10. The method of claim 1, wherein the second correlation also includes a correlation between a fractional weight boiling temperature for a brightstock raffinate and a mutagenicity index value.

11. The method of claim 1, wherein the distillation cut point is selected based on a 95% confidence interval of the linear correlation slope for the first correlation.

12. The method of claim 1, wherein the distillation cut point is selected based on a 95% confidence interval of the linear correlation slope for the second correlation.

13. A method for producing a brightstock extract, the method comprising:
  selecting a distillation cut point temperature between a resid fraction and one or more distillate fractions, the distillation cut point temperature corresponding to a mutagenicity index value of 0.5 or less for a brightstock extract formed from the resid fraction, the distillation cut point temperature being based on,
    (a) a first correlation between a fractional weight boiling temperature for a vacuum resid fraction and a distillation cut point temperature for separating the vacuum resid fraction from a feedstock,
    (b) a second correlation between a fractional weight boiling temperature for a brightstock extract derived from the vacuum resid fraction, and the fractional weight boiling temperature for the vacuum resid fraction, wherein the second correlation has a linear correlation slope of 0.90 or less, and
    (c) a third correlation between the fractional weight boiling temperature for the brightstock extract and a mutagenicity index value;
  distilling a feedstock to separate one or more distillate fractions from a resid fraction at the selected distillation cut point temperature;
  passing at least a portion of the separated resid fraction through a deasphalting unit to produce at least a deasphalted oil fraction; and
  passing the deasphalted oil fraction through a solvent extraction unit to produce at least a brightstock extract having a mutagenicity index value of 0.5 or less.

14. The method of claim 13, wherein the distillation cut point temperature is selected based on a mutagenicity index value for the brightstock extract of less than 0.4.

15. The method of claim 13, wherein the third correlation has a linear correlation slope of at least −0.015.

16. The method of claim 13, wherein the third correlation also includes a correlation between a fractional weight boiling temperature for a deasphalted oil and a mutagenicity index value.

17. The method of claim 13, wherein the third correlation also includes a correlation between a fractional weight boiling temperature for a brightstock raffinate and a mutagenicity index value.

18. The method of claim 13, wherein the distillation cut point is selected based on a 95% confidence interval of the linear correlation slope for the first correlation.

19. The method of claim 13, wherein the distillation cut point is selected based on a 95% confidence interval of the linear correlation slope for the third correlation.

* * * * *